United States Patent

Bredereck et al.

[11] 4,048,315
[45] Sept. 13, 1977

[54] PREPARATION OF NEW 1,3-IDENTICALLY SUBSTITUTED-TRIAZINE-2,4-DIONES

[75] Inventors: Hellmut Bredereck, Stuttgart; Willi Kantlehner, Aalen-Dewangen; Wolfgang Kugel, Stuttgart; Edgar Möhring, Berg. Gladbach; Peter Roessler, Bensberg, all of Germany

[73] Assignee: Bayer Aktiengesellschaft, Leverkusen, Germany

[21] Appl. No.: 722,300

[22] Filed: Sept. 9, 1976

[30] Foreign Application Priority Data

Sept. 30, 1975 Germany .............................. 2543497
July 9, 1976 Germany .............................. 2630849

[51] Int. Cl.$^2$ .................... C07D 251/20; A61L 13/00; A01N 9/22
[52] U.S. Cl. ....................................... 424/249; 544/223
[58] Field of Search .................. 260/248 NS; 424/247

[56] References Cited

U.S. PATENT DOCUMENTS 3,873,540  3/1975  Fuchs et al. .......................... 260/248

Primary Examiner—John M. Ford
Attorney, Agent, or Firm—Burgess, Dinklage & Sprung

[57] ABSTRACT

New 1,3-identically substituted-triazine-2,4-diones of the formula

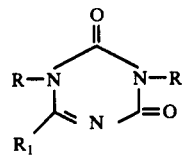

(I), in which
R is alkyl with 2 to 6 carbon atoms, cycloalkyl with 5 or 6 carbon atoms, phenyl, naphthyl, or phenyl or naphthyl substituted by halogen, nitro or alkyl with 1 to 4 carbon atoms, and
R$^1$ is hydrogen or alkyl with 1 to 4 carbon atoms, which possess arthropodicidal and nematicidal properties, are prepared by reacting a bis-silylated carboxylic acid amide of the formula

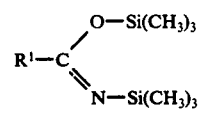

(II)

with an isocyanate of the formula

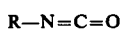

R—N=C=O          (III)

13 Claims, No Drawings

PREPARATION OF NEW 1,3-IDENTICALLY SUBSTITUTED-TRIAZINE-2,4-DIONES

The present invention relates to and has for its objects the provision of particular new 1,3-identically substituted-triazine-2,4-diones which possess arthropodicidal and nematicidal properties, active compositions in the form of mixtures of such compounds with solid and liquid dispersible carrier vehicles, and methods for producing such compounds and for using such compounds in a new way especially for combating pests, e.g. arthropodes and nematodes, with other and further objects becoming apparent from a study of the within specification and accompanying examples.

It has been disclosed by H. Bredereck, F. Effenberger and A. Hofmann in Angew. Chemie, volume 74, page 354 (1962) that the reaction of urea with triethyl-orthoformate gives unsubstituted symmetrical triazine-2,4-dione. However, only unsubstituted triazine-2,4-diones are producible by this process.

It has furthermore been disclosed that the reaction of appropriately substituted biurets with triethyl orthoformate gives 1,3-disubstituted symmetrical triazine-2,4-diones (A. Piskala and J. Gut, Chemical Abstracts, volume 56, 4,766 b). However, this process is restricted to the preparation of 1,3-disubstituted triazine-2,4-diones and is thus not universally applicable.

The preparation of 1,3,6-trimethyltriazine-2,4-dione by alkylation of 6-methyl-triazine-2,4-dione by means of dimethyl sulfate has also been disclosed (G. Ostrogovich and M. Safta, Chemical Abstracts, volume 78, 84, 369y). In this process, however, 6-methyl-triazine-2,4-dione must first be prepared as the starting material and is then alkylated in a second stage. This process gives an unsatisfactory overall yield and is unsuitable for commercial implementation.

It has further been disclosed that 1,3-dimethyltriazine-2,4-dione is produced by thermal rearrangement of 2,4-dimethyloxy-1,3,5-triazine (A. Piskala and J. Gut, Chemical Abstracts, volume 62, 624 g). The yield of this reaction, which takes place at 220° C, is, however, also unsatisfactory, since numerous by-products are formed. Furthermore, the reaction is restricted to the stated compound and does not permit the preparation of other substituted triazine-2,4-diones. Accordingly, this process also is unsuitable for the economical preparation of substituted triazine-2,4-diones.

The present invention now provides, as new compounds, the 1,3-identically substituted triazine-2,4-diones of the general formula

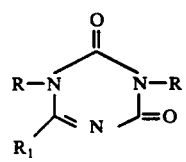

(I), in which
R is alkyl with 2 to 6 carbon atoms, cycloalkyl with 5 or 6 carbon atoms, phenyl, naphthyl, or phenyl substituted by halogen, nitro or alkyl with 1 to 4 carbon atoms, and
$R^1$ is hydrogen or alkyl with 1 to 4 carbon atoms, Preferably R is phenyl, naphthyl, or phenyl substituted by chlorine, methyl or nitro, and $R^1$ is hydrogen, methyl, ethyl, n-propyl or isopropyl.

The present invention also provides a process for the preparation of 1,3 identically substituted triazine-2,4-diones, in which a bis-silylated carboxylic acid amide of the general formula

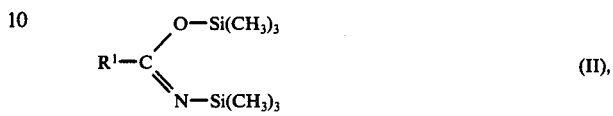

(II), in which
$R^1$ has the abovementioned meaning, is reacted with an isocyanate of the general formula $$R-N=C=O \qquad (III),$$

in which
R is alkyl with up to 6 carbon atoms, cycloalkyl with 5 or 6 carbon atoms, phenyl, naphthyl, or phenyl or naphthyl substituted by halogen, nitro or alkyl with 1 to 4 carbon atoms,
if appropriate in the presence of a diluent.

The reaction of bis-silylated carboxylic acid amides with isocyanates is novel and gives 1,3-identically substituted triazine-2,4-diones. It was surprising and not foreseeable that the 1,3-identically substituted triazine-2,4-diones, which had not previously been obtained, can be prepared in such a simple manner, and in high yield, by this reaction. The process is distinguished by choosing relatively simple, readily available and easily handled starting compounds. It permits the preparation of both 1,3-disubstituted triazine-2,4-diones and the preparation of 1,3,6-trisubstituted triazine-2,4-diones. In contrast thereto, the known processes for the preparation of compounds of this type permit either only the preparation of the corresponding 1,3-disubstituted compounds or only the preparation of the 1,3,6-trimethyl-substituted compound.

Furthermore, the process according to the invention can give the new 1,3-identically substituted triazine-2,4-diones in good yield. Accordingly, the process according to the invention permits the economical preparation of the new substituted triazine-2,4-diones.

It was furthermore surprising that the compounds obtainable in accordance with the process of the invention exhibit an excellent development-inhibiting activity, since such an action was not known for the known compounds of this type. All that was known was that 1,3-dimethyltriazine-2,4-dione possesses some bactericidal activity.

If bis-trimethylsilylformamide and phenyl isocyanate are used as starting materials, the course of the reaction can be represented by the following equation:

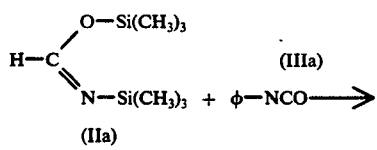

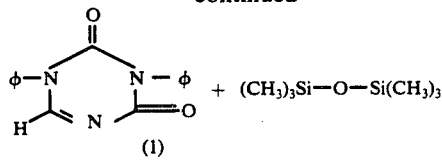

(1)

in which φ represents phenyl.

The structure of bis-trimethyl-silylformamide has not yet been clarified unambiguously. It is conceivable that this compound is also present as N,N-bis-trimethylsilyl-formamide.

Bis-trimethylsilylformamide is the particularly preferred starting compound of the general formula (II). The compounds of the general formula (II) are known.

Particularly preferred starting compounds of the general formula (III) are phenyl, 3-chlorophenyl, 4-chlorophenyl and 3,4-dichlorophenyl isocyanates. The compounds of the general formula (III) are known.

The reaction according to the invention is preferably carried out in the presence of inert organic diluents. As such, it is possible to use aliphatic, aromatic and optionally chlorinated hydrocarbons, for example benzene, toluene, xylene, benzine, methylene chloride, chloroform, carbon tetrachloride and chlorobenzene; ethers, such as diethyl, dibutyl ether and dioxane; ketones, such as acetone, methyl ethyl, ethyl isopropyl and methyl isobutyl ketone; and nitriles, such as acetonitrile.

The reaction can be carried out under normal pressure. The reaction temperature can vary within wide ranges. In general, the reaction is carried out at between about 10° and 150° C, preferably between about 35° and 100° C. The starting materials are generally employed in approximately equimolar amounts, although variations therefrom are still operative but less economical.

The active compounds are well tolerated by plants and have a favorable level of toxicity to warm-blooded animals, and are suitable for combating pests, especially insects, spidermites and nematodes which are encountered in agriculture, in forestry, in the protection of stored products and of materials, and in the hygiene field. They are active against normally sensitive and resistant species and against all or some stages of development.

The above-mentioned pests include: from the class of the Isopoda, for example *Oniscus asellus, Armadillidium vulgare* and *Porcellio scaber;* from the class of the Diplopoda, for example, *Blaniulus guttulatus;* from the class of the Chilopoda, for example *Geophilus carpophagus* and Scutigera spec; from the class of the Symphyla, for example *Scutigerella immaculata;* from the order of Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example Forficula auricularia; from the order of the Isoptera, for example Reticulitermes spp.; from the order of the Anoplura, for example *Phylloxera vastatrix, Pemphigus* spp., Pediculus humanus corporis, Haematopinus spp. and Linognuthus spp.; from the order of the Mallophaga, for example Trichodectes spp. and Damalinea spp.; from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and *Triatoma* spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia cleae, Laodelphax striatellus, Nilaparvata lugens, Aonidiella aurantii, Aspidiotus hederae,* Pseudococcus spp. and Psylla spp.; from the order of the Lepidoptera, for example *Pectinophora gossypiella, Bupalus piniarius, Cheimatobia brumata, Lithocolletis blancardella, Hyponomeuta padella, Plutella maculipennis, Malasocoma neustria, Euproctis chrysorrhoea, Lymantria* spp., *Bucculatrix thurbella, Phyllocnistis citrella, Agrotis* spp., Euxoa spp., Feltia spp., *Earias insulana, Heliothis* spp., *Laphygma exigua, Mamestra brassicae, Panolis flammea, Prodenia litura,* Spodoptera spp., Trichoplusia ni, *Carpocapsa pomonella, Pieris* spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., Sitophilus spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus holoeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.; from the order of the Diptera, for example Aedes spp., Anopheles spp., Culex spp., *Drosophila melanogaster, Musca* spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oxcinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.; from the class of the Arachnida, for example *Scorpio maurus* and *Latrodectus mactans;* from the order of the Acarina, for example *Acarus siro,* Argas spp., Ornithororos spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chlorioptes spp., Sarcoptes spp., Tarsonemus spp., *Bryobia praetiosa, Panonychus* spp. and Tetranychus spp.

The plant-parasitic nematodes include Pratylenchus spp., *Radopholus similis, Ditylenchus dipasaci, Tylenchulus semipenetrans,* Heterodera spp., Meloidogyne spp., Aphelenchoides spp., Longidorus spp., Xiphinema spp. and Trichodorus spp..

To boost and supplement their spectrum of action, the active compounds according to the invention can, depending on the intended use, be combined with other insecticidal active compounds. In particular, the active compounds mentioned below and other members of the groups of active compounds represented by these active compounds are suitable for this purpose.

Organic phosphorus compounds, such as O,O-dimethyl-S-isopropyl-2-sulfinylethylthiophosphate, O,O-dimethyl-S-(2-methoxyethyl-acetamide)-dithiophosphate (Medithionat), O,O-diethyl-S-(N-ethoxycarbonyl-N-methylcarbmoylmethyl)-dithiophosphate (Mecarbam), S-(5-methoxy-4-pyron-2-yl-methyl)-O,O-dimethylthiophosphate, O,S-dimethyl-N-acetyl-amidothiophosphate (Acephate), 1-phenyl-3-(diethoxy-thiophosphoryloxy)-1,2,4-triazole (Triazophos), O,O-diethyl-O-[6-(3(2-phenyl)-pyridazinonyl)]thiophosphate, 4-dimethoxy-thiophosphoryloxy)-2-diethylamino-6-methylpyrimidine (Pirimiphos-Methyl), 4-diethoxy-thiophosphoryloxy)-2-diethylamino-6-methyl-pyrimidine (Pirimiphos-Ethyl), O,O-diethyl-O-(3-chloro-7-methyl-2-pyrazolo[1,5-α]-pyrimidinyl)-thiophosphate (Chlorpyrophos), O-ethyl-S-n-propyl-O-(2,4-dichlorophenyl)-thiophosphate (Dichlorpropafos), O-ethyl-O(4-methylmercaptophenyl)-S-n-propyldithiophosphate (Mercaptopropafos), O-ethyl-O-(2-carbisopropoxyphenyl)-isopropyl-amidothiophosphate (Isofenphos), S-chloromethyl-diethyl-phosphorthiolothionate (Chlormephos), S-(tert.-butylthio)methyl-O,O-diethyldithiophosphate, O,O-diethyl-O-[O-chlorophenyl)-glyoxylonitrile-oxime]-thiophosphate (Chlorphoxim), O,O-diethyl-O-phenylglyoxylonitrile-oxymethiophosphate (Methylphoxim), bis-O,O-diethyl-phosphoric acid anhydride (TEPP), dimethyl-(2,2,2-trichloro-1-hydroxyethyl) phosphonate (Trichlorfon), 1,2-dibromo-2,2-dichloroethyldimethylphosphate (Naled), 2,2-dichlorovinyldimethylphosphate (Dichlorvos), 2-methoxycarbamyl-1-methylvinyldimethylphosphate (Mevinphos), dimethyl-1-methyl-2-(methylcarbamoyl)-vinylphosphate cis (Monocrotophos), 3-(dimethoxyphosphinyloxy)-N,N-dimethyl-cis-crotonamide (Dicrotophos), 2-chloro-2-diethylcarbamoyl-1-methylvinyldimethylphosphate (Phosphamidon), O,O-diethyl-O (or S)-2-(ethylthio)-ethylthiophosphate (Demeton), S-ethylthioethyl-O,O-dimethyl-dithiophosphate (Thiometon), O,O-diethyl-S-ethylmercaptomethyldithiophosphate (Phorate), O,O-diethyl-S-2-ethylthioethyl-dithiophosphate (Disulfoton), O,O-dimethyl-S-2-(ethylsulfinyl)ethylthiophosphate (Oxydemeton-methyl), O,O-dimethyl-S-(1,2-dicarbethoxyethyl-dithiophosphate (Malathion), O,O,O,O-tetraethyl-S,S'-methylene-bis-dithiophosphate (Ethion), O-ethyl-S,S-dipropyldithiophosphate (Prophos), O,O-dimethyl-S-(N-methyl-N-formylcarbamoylmethyl)-dithiophosphate (Formothion), O,O-dimethyl-S-(N-methylcarbamoylmethyl)-dithiophosphate (Dimethoat), O,O-dimethyl-O-p-nitrophenylthiophosphate (Parathion-methyl), O,O-diethyl-O-p-nitrophenylthiophosphate (Parathion), O-ethyl-O-p-nitrophenylphenylthiophosphonate (PEN), O,O-dimethyl-O-(4-nitro-m-tolyl)thiophosphate (Fenitrothion), O,O-dimethyl-O-2,4,5-trichlorophenylthiophosphate (Ronnel), O-ethyl-O-2,4,5-trichlorophenylethylthiophosphonate (Trichloronat), O,O-dimethyl-O-2,5-dichloro-4-bromophenylthiophosphate (Bromophos), O,O-dimethyl-O-(2,5-dichloro-4-iodophenyl)-thiophosphate (Iodofenphos), 4-tert.-butyl-2-chlorophenyl-N-methyl-O-methylamidophosphate (Crufomat), O,O-dimethyl-O-3-(3-methyl-4-methylmercaptophenyl)thiophosphate (Fenthion), isopropylamido-O-ethyl-O-(4-methylmercapto-3-methylphenyl)-phosphate (Phenamiphos), O,O-diethyl-O-p-(methylsulfinyl)-phenylthiophosphate (Fensulfothion), O-p-(dimethylsulfamido)phenyl-O,O-dimethylthiophosphate (Famphur), O,O,O',O'-tetramethyl-O,O'-thiodi-p-phenylenethiophosphate, O-ethyl-S-phenylethyldithiophosphonate (Fonofos), O,O-dimethyl-O-(α-methylbenzyl-3-hydroxycrotonyl)phosphate, 2-chloro-1-(2,4-dichlorophenyl)vinyl-diethylphosphate (Chlorfenvinphos), 2-chloro-1-(2,4,5-trichlorophenyl)vinyl-dimethylphosphate, O-[2-chloro-1-(2,5-dichlorophenyl)]vinyl-O,O-diethylthiophosphate, phenylglyoxylonitrile-oxime-O,O-diethylthiophosphate (Phoxim), O,O-diethyl-O-(3-chloro-4-methyl-2-oxo-2-H-1-benzopyran-7-yl)-thiophosphate (Coumaphos), 2,3-p-dioxanedithiol-S,S-bis(O,O-diethyldithiophosphate) (Dioxathion), 5-[(6chloro-2-oxo-3-benzoxazolinyl)-methyl]-O,O-diethyldithiophosphate (Phosalon), 2-(diethoxyphosphinylimino)-1,3-dithiolane (Phosfolan), O,O-dimethyl-S-[2-methoxy-1,3,4-thiadiazol-5-(4H)-onyl-(4)-methyl]dithiophosphate (Methidathion), O,O-dimethyl-S-phthalimidomethyldithiophosphate (Imidan), O,O-diethyl-O-(3,5,6-trichloro-2-pyridyl)thiophosphate (Chlorpyrifos), O,O-diethyl-O-2-pyrazinylthiophosphate (Thionazin), O,O-diethyl-O-(2-isopropyl-4-methyl-6-pyrimidyl)-thiophosphate (Diazinon), O,O-diethyl-O-(2-quinoxalyl)-thiophosphate (Quinalphos), O,O-dimethyl-S-(4-oxo-),2,3-benzotriazin-3-(4H)-yl-methyl)-dithiophosphate (Azinphosmethyl), O,O-diethyl-S-(4-oxo-1,2,3-benzotriazin-3(4H)-yl-methyl)-dithiophosphate (Azinphosethyl), S-[(4,6-diamino-s-triazin-2-yl)-methyl]-O,O-dimethyldithiophosphate (Menazon), O,O-dimethyl-O-(3-chloro-4-nitrophenyl)thiophosphate (Chlorthion), O,O-dimethyl-O (or S)-2-(ethylthioethyl)thiophosphate (Demeton-S-Methyl), 2-(O,O-dimethyl-phosphorylthiomethyl)-5-methoxypyrone-4-3,4-dichlorobenzyl-triphenylphosphonium chloride, O,O-diethyl-S-(2,5-dichlorophenyl-thiomethyl)dithiophosphate (Phenkapton), 5-azino-bis(-dimethylamido)phosphinyl-3-phenyl-1,2,4-triazole (Triamiphos), N-methyl-5-(O,O-dimethylthiolphosphoryl)-3-thiavaleramide (Vamidothion), O,O-dimethyl-S-(methylcarbamoylmethyl)-thiophosphate (Omethoat), O-ethyl-O-(8-quinolinyl)-phenylthiophosphonate (Oxinothiophos), O-methyl-S-methyl-amidothiophosphate (Methamidophos), O-methyl-O-(2,5-dichloro-4-bromophenyl)-benzothiophosphonate (Phosvel), O,O-diethyl-S-(N-isopropylcarbamoylmethyl)-dithiophosphate (Prothoat), S-N-(1-cyano-1-methylethyl)carbamoylmethyldiethylthiolphosphate (Cyanthoat), S-(2-acetamidoethyl)-O,O-dimethyldithiophosphate, O,O-dimethyl-O-(2-chloro-4-nitrophenyl)-thiophosphate (Dicapthon), O,O-dimethyl-O-p-cyanophenyl-thiophosphate (Cyanox), O-ethyl-O-p-cyanophenyl-thiophosphonate, O,O-diethyl-O-2,4-dichlorophenylthiophosphate (Dichlorfenthion), O,O-diethyl-O-2,5-dichloro-4-bromophenylthiophosphate (Bromophosethyl), dimethyl-p-(methylthio)-phenylphosphate, O,O-dimethyl-O-p-sulfamido-phenylthiophosphate, O-[p-(p-chlorophenyl)-azophenyl]-O,O-dimethylthiophosphate (Azothoat), O,O-dimethyl-S-p-chlorophenylthiophosphate, O,O-dimethyl-S-(p-chlorophenylthiomethyl)-dithiophosphate (Methylcarbophenothion), O,O-diethyl-p-chlorophenylmercaptomethyl-dithiophosphate (Carbophenothion), O,O-diethyl-S-p-chlorophenylthiomethyl-thiophosphate, O,O-dimethyl-S-(carbethoxy-phenylmethyl)-dithiophosphate (Phenthoat), O,O-diethyl-7-hydroxy-3,4-tetramethylene-coumarinyl-thiophosphate (Coumithoat), 2-methoxy-4-H-1,3,2-benzodioxaphosphorine-2-sulfide, S-(2-chloro-1-phthalimidoethyl)-O,O-diethyldithiophosphate (Dialiflor), N-hydroxynaphthalimidodiethylphosphate, O,O-dimethyl-O-(3,5,6-trichloro-2-pyridyl)-thiophosphate, S-2-(ethylsulfonyl) ethyl-dimethylthiophosphate (Dioxydemeton-S-Methyl), diethyl-S-2-(ethylsulfinyl)-ethyl-dithiophosphate (Oxydisulfoton), bis-O,O-diethylthiophosphoric acid anhydride (Sulfotep), dimethyl-1,3-di(carbomethoxy)-1-propen-2-yl phosphate, dimethyl-(2,2,2-trichloro-1-butyroyloxyethyl) phosphonate (Butonat), dimethyl-N-methoxymethylcarbamoylmethyl-dithiophosphate (Formocarbam), O-ethyl-S,S-diphenyldithiolphosphate (Ediphenphos), diisopropylaminofluorophosphate (Mipafox), O,O-dimethyl-S-(morpholinylcarbamoylmethyl)dithiophosphate (Morphothion), octamethylpyrophosphoramide (Schradan), N,N,N',N'-tetramethyldiamidofluorophosphate (Dimefox), O-methyl-O-(2-carboisopropoxyphenyl)-amidothiophosphate (Isocarbophos), as well as nitrophenols and their derivatives, such as the Na salt of 4,6-dinitro-2-methylphenol[dinitrocresol], the 2,2',2"-triethanolamine salt of dinitrobutylphenol, 2-(1-methylheptyl)-4,6-dinitrophenylcrotonate [Dinocap], 2-sec.-butyl-4,6-dinitrophenyl-3-methylbutenoate [Binapacryl] and 2-sec.-butyl-4,6-dinitrophenyl isopropylcarbonate [Dinobuton], as well as dichlorodiphenyltrichloroethane (DDT), 2,2-bis-(p-chlorophenyl)-1,1-dicloroethane (TDE), bis-(p-chlorophenyl)-trichloroethanol (Dicofol), ethyl-4,4'-dichlorodiphenylglycolate (Chlorbenzilate), isopropyl-4,4'-dichlorobenzilate (Chloropropylate), isopropyl-4,4'-dibromobenzilate (Phenisobromolate), 1,1,1-trichloro-2,2-bis(p-methoxyphenyl)-ethane (Methoxychlor), 1,1-bis(p-ethylphenyl)-2,2-dichloroethane (Perthane), bis-(4-chlorophenyl)-cyclopropylcarbinol (Kilacar), dichlorophenylbenzeneslfonate (Genite), 4-chlorophenyl-2,4,5-trichlorophenyl-azosulfide (Milbex), 2-(p-tert.-butylphenoxy)-isopropyl 2'-chloroethyl sulfite (Aracide), 2-(p-tert.-butylphenoxy)-cyclohexyl 2-propinyl sulfite (Omite), 2-fluoro-N-methyl-N-1-naphthylacetamide (Nissol), N-dichlorofluoromethylthio-dimethylaminosulfonic acid anilide (Dichlofluanid), N-[(dichlorofluoromethyl)-thio]-N',N'-dimethyl-N-p-tolylsulfamide (Tolylfluanid), 1,2-dibromo-3-chloropropane (DBCP), 1,5-bis-(2,4-dimethylphenyl)-3-methyl-1,3,5-triazapenta-1,4-diene (Amitraz), ethyl-O-benzoyl-3-chloro-2,6-dimethoxybenzohydroximate (Benzomate), tricyclohexyl-tin hydroxide (Plictran), 1-tricyclohexylstannyl-1,2,4-triazole (Tricyclazol), torque (Neostanox), isopropyl-11-methoxy-3,7,11-trimethyldodeca-2,4-dienoate (Altosid), ethyl-3,7,11-trimethyl-2,4-dodecadienoate (Altozar), 2,2,2-trichloro-1-(3,4-dichlorophenyl)-ethanol acetate (Dichlorfenat), pyrethrin I, pyrethrin II, 3-allyl-2-methyl- b 4-oxo-2-cylopenten-1-yl chrysanthemumate (Allethrin), 6-chlorperonyl chrysanthemumate (Barthrin), 2,4-dimethylbenzylchrysanthemumate (Dimethrin), 2,3,4,5-tetrahydrophthalimidomethyl chrysanthemumate, 6-methyl-2-oxo-1,3-dithiolo-[4,5-b]-quinoxaline (Quinomethionat), (1)-3-(2-furfuryl)-2-methyl-4-oxocyclopent-2-en-1-yl-(cis + trans) chrysanthemum-monocarboxylate (Furethrin), 4-chlorobenzyl-4-fluorophenyl sulfide (Fluorbenside), 5,6-dichloro-1-phenoxycarbanyl-2-trifluoromethylbenzimidazole (Fenozaflor), p-chlorophenyl p-chlorobenzenesulfonate (Ovex), p-chlorophenyl benzenesulfonate (Fenson), p-chlorophenyl-2,4,5-trichlorophenylsulfone (Tetradifon), p-chlorophenyl-2,4,5-trichlorophenyl sulfide (Tetrasul), p-chlorobenzyl-p-chlorophenyl sulfide (Chlorbenside), 2-thio-1,3-dithiolo-(5,6)quinoxaline (Thiochinox), prop-2-ynyl-(4-1-butylphenoxy)-cyclohexyl sulfite (Propargil), 1-dimethyl-2-(2'-methyl-4'-chlorophenyl)-formamidine (Chlorphenamidin) and also ureas such as 1-(2,6-dichlorobenzoyl)-3-(3,4-dichlorophenyl)-urea (DU 19,111), 1-(2,6-dichlorobenzoyl)-3-(4-chlorophenyl)-urea (pH 60-38), 1-(2,6-difluorobenzoyl)-3-(4-chlorophenyl)-urea (pH 60-40) and N-2-methyl-4-chlorophenyl-N',N'-dimethyl-thiourea, and carbamates such as 2-methylthio-O-(N-methyl-carbamoyl)butanone-3-oxime (Butocarboxim) = Blumi, (2-ethylmercaptomethylphenyl)-N-methylcarbamate (Ethiophencarb), 1-dimethyl-carbamoyl-N-(methylcarbamoyloxy)-thioformhydroxime-acid methyl ester (Oxamyl) = Vydate, 2,2-dimethyl-1,3-benzodioxol-4-yl-N-methylcarbamate (Bendoxicarb), 1-naphthyl-N-methyl-carbamate (Carbaryl), 4-dimethylamino-3,5-xylyl-N-methyl-carbamate, 4-dimethylamino-3-tolyl-N-methyl-carbamate (Aminocarb), 4-methylthio-3,5-xylyl-N-methyl-carbamate (Methiocarb), 3,4,5-trimethylphenyl-N-methyl-carbamate, 2-chlorophenyl-N-methylcarbamate (CPMC), 5-chloro-6-oxo-2-norbornane-carbonitrile-O-(methylcarbamoyl)-oxime, 1-(dimethylcarbamoyl)-5-methyl-3-pyrazolyl-N,N-dimethyl-carbamate (Dimetilan), 2,3-dihydro-2,2-dimethyl-7-benzofuranyl-N-methyl-carbamate (Carbofuran), 2-methyl-2-methylthio-propionaldehyde-O-(methylcarbamoyl)-oxime (Aldicarb), N-(1-ethylpropyl)phenyl-N-methyl-carbamate, 3,5-di-tert.-butyl-N-methyl-carbamate, N-(1-methylbutyl)phenyl-N-methyl-carbamate, 2-isopropylphenyl-N-methyl-carbamate (Isoprocarb), 2-sec.-butylphenyl-N-methyl-carbamate, 3-isopropyl-5-methylphenyl-N-methyl-carbamate (Promecarb), 2-(1,3-dioxalan-2-yl)-phenyl-N-methyl-carbamate (Dioxacarb), 2-isopropoxy-phenyl-N-methyl-carbamate (Arprocarb), 4-diallylamino-3,5-xylyl-N-methyl-carbamate (Allyxicarb), 2,3-dihydro-2-methyl-7-benzofuranyl-N-methyl-carbamate (Decarbofuran), 1-isopropyl-3-methylpyrazol-5-yl-N,N-dimethyl-carbamate (Isolan), 2-dimethylamino-5,6-dimethylpyrimidin-4-yl-N,N-dimethylcarbamate (Pirimicarb), 3,4-dimethylphenyl-N-methyl-carbamate, 3-dimethylamino-methyleneiminophenyl-N-methyl-carbamate (Formetanate) and its salts, 1-methylthioethyl-imino-N-methylcarbamate (Methomyl), 1,3-bis(carbamoylthio)-2-(N,N-dimethylamino)-propane hydrochloride and 5,5-dimethylhydroresorcinol dimethyl-carbamate, and chlorinated hydrocarbons, such as 6,7,8,9,10,10-hexachloro-1,5,5a,6,9,9a-hexahydro-6,9-methane-2,4,3-benzodioxathiepine-3-oxide (Endosulfan), chlorinated camphene with 67-69% chlorine content (Toxaphen), chlorinated terpenes (Strobane), 1,2,3,5,6,7,8,9,10, 10-decachloro-pentacyclo-[5.2.1.0$^{2.6}$.0$^{3.9}$.0$^{5.8}$]-decan-4-one (Chlordecone), dodecachlorooctahydro-1,3,4-methano-2H-cyclobuta[cd]pentalene (Mirex), decachloro-bi-2,4-cyclopentadien-1-yl (Dekaflor), ethyl-1,1a,3,3a,4,5,5,5a,5b,6-decachlorooctahydro-2-hydroxy-1,3,4-metheno-2H-cyclobuta[cd]-pentalene 2-laevulinate (Kelevan), γ-hexachlorocyclohexane (Gammexane; Lindane; γHCH), 1,2,4,5,6,7,8,8-octachloro-3a,4,7,7a'-tetrahydro-4,7-methylene-indane (Chlordan), 1,4,5,6,7,8,8-heptachloro-3a,4,7,7a-tetrahydro-4,7-methyleneindane (Heptachlor) and 1,2,3,4,10,10-hexachloro-6,7-epoxy-1,4,4a,5,6,7,8,8a-octahydro-endo-endo-5,8-dimethano-naphthalene (Endrin), as well as pheromones, synergistic agents, repellents, active compounds of vegetable origin, products of the metabolism of microorganisms and development inhibitors.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, foams, wettable powders, aerosols, seed-treatment powders, natural and snthetic materials impregnated with active compound, very fine capsules in polymeric substances and in coating compositions, for use on seed, and in formulations used with burning equipment, such as fumigating cartridges, fumigating cans, fumigating coils and the like, as well as ULV cold mist and warm mist formulations, etc.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives, such as carboxymethylcellulose and natural and synthetic polymers in the form of powders, granules or latex, such as gum arabic, polyvinyl alchol and polyvinyl acetate, can be used in the formulations.

Colorants, such as inorganic pigments, for example iron oxide, titanium oxide, Prussian blue and organic dyestuffs, such as alizarine and azo-metal phthalocyanine dyestuffs, and trace nutrients such as salts of iron, manganese, boron, copper, cobalt, molybdenum and zinc, can also be used.

Such active compounds may be employed alone or in the form of mixtures with one another and/or with such solid and/or liquid dispersible carrier vehicles and/or with other known compatible active agents, especially plant protection agents, such as other arthropodicides and nematicides, or fungicides, bactericides, rodenticides, herbicides, fertilizers, growth-regulating agents, etc., if desired, or in the form of particular dosage preparations for specific application made therefrom, such as solutons, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100%, preferably 0.01–10% by weight the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used gainst nematodes, the preparations are generally applied to an area of agriculture in amounts of 1 to 100 kg of active compound per hectare, and are then incorporated into the soil.

When used against pests harmful to health and pests of stored products, the active compounds are distinguished by an excellent residual action on wood and clay, as well as a good stability to alkali on limed substrates. The compounds also exhibit relatively low mammalian toxicity.

When used at high concentrations, the compounds according to the invention show also a certain herbicidal action.

The present invention also contemplates methods of selectively killing, combating or controlling pests, e.g. arthropods (for example, insects and acarids) and nematodes, which comprises applying to at least one of correspondingly (a) such arthropods, (b) such nematodes, and (c) the corresponding habitat thereof, i.e. the locus to be protected, e.g. to a growing crop, to an area where a crop is to be grown or to a domestic animal, a correspondingly combative or toxic amount, i.e. an arthropodically or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the examples hereinbelow. These examples show the arthropod metamorphosis-inhibiting action of the compounds according to the invention, without implying a limitation with regard to the breadth of action of these compounds. In these experiments, the morphological changes, such as half-formed pupae, incompletely emerged larvae or caterpillars, defective wings, pupal cuticules in imagines, and mortality, are assessed throughout the entire stated development of the test animals. The sum of the morphological malformations and of the mortality during development are stated in percent of the number of test animals.

EXAMPLE 1

Metamorphosis-inhibiting action/ingestion test

Test insects: *Plutella maculipennis* (caterpillars in the 4th stage of development) - 20 insects *Phaedon cochleariae* (larvae in the 4th stage of development) - 20 insects Feed plants: Cabbage plants (*Brassica oleracea*)

Solvent: 10 parts by weight of dimethylformamide

Emulsifier: 1 part by weight of polyoxyethylenesorbitane monolaurate.

To produce a suitable preparation of active compound, 2 parts by weight of active compound were mixed with the stated amount of solvent and emulsifier and with sufficient water to give a 1% strength mixture which was diluted with water to the desired concentration.

The test insects were fed with leaves of the feed plants, which were provided with a uniform spray coating of the active compound mixture of the selected concentration, until the imago developed.

For control, insects were fed with leaves provided only with solvent and emulsifier at the stated concentration. The results can be seen from the table which follows:

Table 1

| Active compound | Test insects: Concentration: | Plutella 0.01% | Phaedon 0.01% |
|---|---|---|---|
| Control | | 0 | 0 |
| (known) | | 20% | 30% |
| (14) | | 100% | 100% |
| (3) | | 60% | 85% |
| (15) | | 85% | / |
|  | | 100% | / |

Table 1-continued
Metamorphosis-inhibiting action/ingestion test

| Active compound | Test insects: Concentration: | Plutella 0.01% | Phaedon 0.01% |
|---|---|---|---|

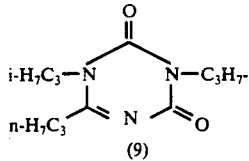

(9)                 100%    /

EXAMPLE 2

Metamorphosis-inhibiting action/Laphygma test

Test insects: Laphygma exigua (caterpillars in the 4th stage of development)

Feed: 1 cm thick discs of 3 cm diameter air-dried compounded feed of shredded beans, yeast, vitamin mixture, powdered leaves, agar and preservative Solvent: 10 parts by weight Emulsifier: 1 part by weight of polyoxyethylene(20-) sorbitane monolaurate.

To produce a suitable preparation of active compound, 2 parts by weight of active compound were mixed with the stated amount of solvent and emulsifier and with sufficient water to give a 1% strength mixture which was diluted with water to the desired concentration.

Each test insects was placed on a separate feed disc, moistened with 1.5 ml of active compound solution of the desired concentration, and was observed until the imago emerged. 5 To 10 test insects were used per test. As the control, test insects were each placed on a separate feed disc moistened with 1.5 ml of solvent and emulsifier of the desired concentration and were observed until the imago emerged. The results can be seen from the table which follows:

Table 2
Metamorphosis-inhibiting action/Laphygma test

| Active compound | Concentration: 0.1% |
|---|---|
| Control | 0 |
| 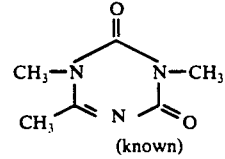 (known) | 20% |
| 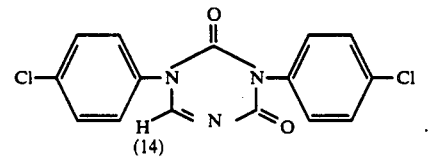 (14) | 100% |
| 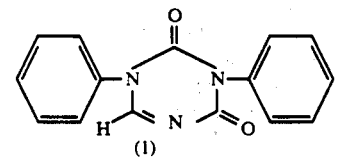 (1) | 50% |

Table 2-continued
Metamorphosis-inhibiting action/Laphygma test

| Active compound | Concentration: 0.1% |
|---|---|
| 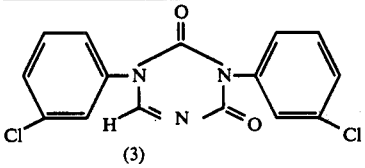 (3) | 80% |
| 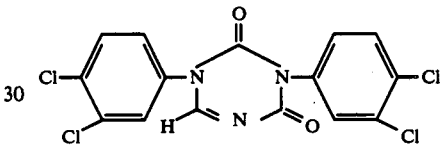 (15) | 90% |
| 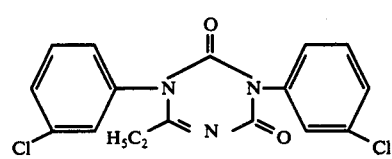 (8) | 80% |

EXAMPLE 3

Metamorphosis-inhibiting action/mosquito test

Test insects: Aëdes aegypti (larvae in the 3rd stage of development) - 20 insects Solvent: 10 parts by weight Emulsifier: 1 part by weight of polyoxyethylene(20-)sorbitan monolaurate To produce a suitable preparation of active compound, 2 parts by weight of active compound were mixed with the stated amount of solvent and emulsifier and with sufficient water to give a mixture which contained 100 ppm of active compound. This was diluted with water to the desired concentration.

The test insects were placed in 90 ml of these active compound solutions and observed until the imago emerged. As the control, test insects were placed in a solvent and emulsifier-water mixture of the stated concentration and observed until the imago emerged.

The results can be seen from the table which follows:

Table 3
Metamorphosis-inhibiting test/mosquito test

| Active compound | Concentration: 10 ppm |
|---|---|
| Control | 0 |

Table 3-continued

Metamorphosis-inhibiting test/mosquito test

| Active compound | Concentration: 10 ppm |
|---|---|
| 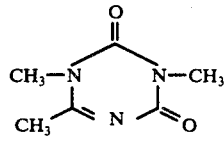 (known) | 60% |
| 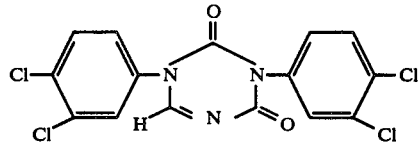 | 80% |
| 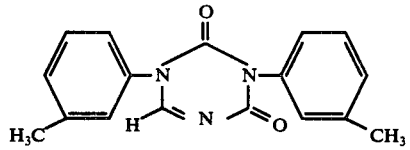 | 100% |
| 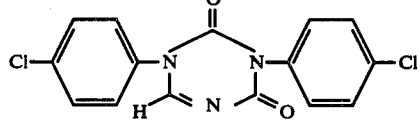 | 100% |
| 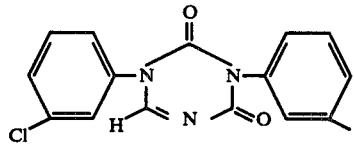 | 85% |

The process of this invention is illustrated by the following preparative Examples.

EXAMPLE 4

Process for the preparation of 1,3-diphenyl-triazine-2,4-dione.

18.9 g (0.1 mole) of bis-trimethylsilylformamide were added dropwise to 23.8 g (0.2 mole) of phenyl isocyanate in 50 ml of ether at a speed such that the solvent just boiled. After the reaction had ended, as could be ascertained by the subsiding of the temperature rise due to the exothermic reaction, the hexamethylsiloxane formed and the solvent were distilled off. The crystals which remained were recrystallized from chloroform. 22.3 g (84.2% of theory) of 1,3-diphenyl-triazine-2,4-dione of melting point 224° C were obtained.

The following compounds were prepared analogously:

Table 4

$$\text{(I)}$$

| Compound | R | R¹ | Melting point °C | (Yield, %) |
|---|---|---|---|---|
| 2 | CH₃—phenyl | H | 167 | 69.5 |
| 3 | Cl—phenyl | H | 171 | 97.4 |
| 4 | phenyl | CH₃ | 246 | 88.5 |
| 5 | Cl—phenyl | CH₃ | 245 | 43.7 |
| 6 | naphthyl | CH₃ | 277 (decomposition) | 69.7 |
| 7 | phenyl | C₂H₅ | 231 | 82.9 |
| 8 | Cl—phenyl | C₂H₅ | 225 | 81.2 |
| 9 | i-C₃H₇ | n-C₃H₇ | 75 | 97 |
| 10 | phenyl | n-C₃H₇ | 206 | 67.2 |
| 11 | Cl—phenyl | n-C₃H₇ | 212 | 29.8 |
| 12 | Cl,Cl—phenyl | n-C₃H₇ | 252 | 38.4 |
| 13 | naphthyl | n-C₃H₇ | 264 | 38.8 |

EXAMPLE 5

Preparation of 1,3-di(parachlorophenyl)-triazine-2,4-dione 18.9 g (0.1 mole) of bis-trimethylsilylformamide were added dropwise to 30.6 g (0.2 mole) of 4-chlorophenyl isocyanate in 50 ml of benzene at a speed such that the solvent just boiled. After the reaction had ended, as can be ascertained by the subsiding of the temperature rise due to the exothermic reaction, the solvent and hexamethylsiloxane formed were distilled off. The crystals which remained were recrystallized from chloroform. 33.1 g of 1,3-di(parachlorophenyl)-triazine-2,4dione of melting point 205° C were obtained.

The following compounds were obtained analogously:

Table 5

| Compound | R | R' | Melting point ° C | (Yield, %) |
|---|---|---|---|---|
| 15 | Cl-⟨⟩-Cl (3,4-dichlorophenyl) | H | 204 | 92.3 |
| 16 | pentachlorophenyl | H | 239 | 94 |
| 17 | CH₃ | C₂H₅ | 70 | 90 |

EXAMPLE 6

Preparation of 1,3-di-n-propyl-triazine-2,4-dione 3.78 g (0.02 mole) of bis-trimethylsilylformamide were slowly added dropwise to 3.4 g (0.04 mole) of n-propyl isocyanate in 5 ml of ligroin at room temperature. The mixture was then stirred for 3 hours at 100° C and cooled slowly, and the crystals which remained were filtered off. 3.47 g of 1,3-di-n-propyl-triazine-2,4-dione of melting point 90° C were obtained.

The following compounds were obtained analogously:

Table 6

| Compound | R | R' | Melting point ° C | (Yield, %) |
|---|---|---|---|---|
| 19 | n-C₄H₉ | H | 89 | 84 |
| 20 | cyclohexyl | H | 101 | 79 |
| 21 | o-tolyl | H | 180 | 79 |
| 22 | 3,5-dimethylphenyl | H | 195 | 84 |

Other compounds which can be similarly prepared include:

Table 7

| Compound | R | R¹ |
|---|---|---|
| 23 | 3-nitro-5-methylphenyl | n-C₄H₉ |

Table 7-continued

| Compound | R | R¹ |
|---|---|---|
| 24 | cyclopentyl | H | and the like.

It will be appreciated that the instant specification and examples are set forth by way of illustration and not limitation, and that various modifications and changes may be made without departing from the spirit and scope of the present invention.

What is claimed is:

1. A 1,3-identically substituted-triazine-2,4-dione of the formula

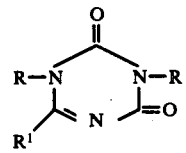

(I)

in which
  each R is the same and is alkyl with 2 to 6 carbon atoms, cycloalkyl with 5 or 6 carbon atoms, phenyl, naphthyl, or phenyl or naphthyl substituted by halogen, nitro or alkyl with 1 to 4 carbon atoms, and
  R¹ is hydrogen or alkyl with 1 to 4 carbon atoms.

2. A compound according to claim 1, in which R is phenyl, naphthyl, or phenyl substituted by chlorine, methyl or nitro, and R¹ represents hydrogen, methyl, ethyl, n-propyl or isopropyl.

3. The compound according to claim 1, wherein such compound is 1,3-di-(m-tolyl)-triazine-2,4-dione of the formula

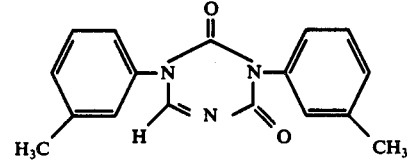

4. The compound according to claim 1, wherein such compound is 1,3-di-(m-chlorophenyl)-6-ethyl-triazine-2,4-dione of the formula

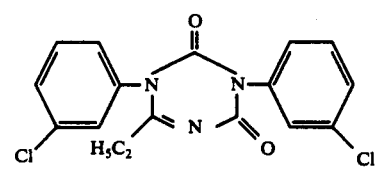

5. The compound according to claim 1, wherein such compound is 1,3-di-isopropyl-6-n-propyl-triazine-2,4-dione of the formula

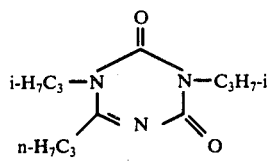

6. The compound according to claim 1, wherein such compound is 1,3-di-(p-chlorophenyl)-triazine-2,4-dione of the formula

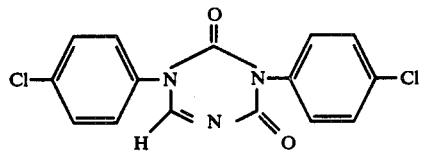

7. The compound according to claim 1, wherein such compound is 1,3-di-(3,4-dichlorophenyl)-triazine-2,4-dione of the formula

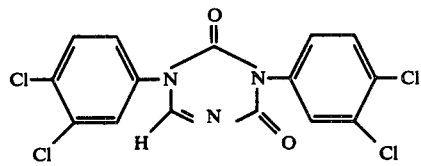

8. A process for the preparation of a 1,3 identically substituted-triazine-2,4-dione, comprising reacting a bis-silylated carboxylic acid amide of the formula

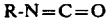

with an isocyanate of the formula

R-N=C=O in which
R is alkyl with up to 6 carbon atoms, cycloalkyl with 5 or 6 carbon atoms, phenyl, naphthyl, or phenyl or naphthyl substituted by halogen, nitro or alkyl with 1 to 4 carbon atoms.

9. A process according to claim 8, in which the reaction is carried out at a temperature between about 0° and 150° C.

10. A process according to claim 8, in which the reaction is carried out at a temperature between about 35° and 100° C in the presence of an inert organic solvent employing substantially equimolar amounts of the reactants.

11. A nematicidal or arthropodicidal composition containing as active ingredient a nematicidally or arthropodicidally effective amount of a compound according to claim 1 in admixture with a diluent.

12. A method of combating nematodes or arthropods which comprises applying to the nematodes or arthropods, or to a habitat thereof, a nematicidally or arthropodicidally effective amount of a compound according to claim 1.

13. The method according to claim 12 in which said compound is
1,3-di-(m-tolyl)-triazine-2,4-dione,
1,3-di-(m-chlorophenyl)-6-ethyl-triazine-2,4-dione,
1,3-di-isopropyl-6-n-propyl-triazine-2,4-dione,
1,3-di-(p-chlorophenyl)-triazine-2,4-dione, or
1,3-di-(3,4-dichlorophenyl)-triazine-2,4-dione.

* * * * *